US007124462B2

(12) United States Patent
Lee

(10) Patent No.: US 7,124,462 B2
(45) Date of Patent: Oct. 24, 2006

(54) TOOTHBRUSH WITH MOVING BRISTLE

(76) Inventor: Jen-Feng Lee, 17800 Castleton St., Suite 383, City of Industry, CA (US) 91748

( * ) Notice: Subject to any disclaimer, the term of this patent is extended or adjusted under 35 U.S.C. 154(b) by 314 days.

(21) Appl. No.: 10/711,046

(22) Filed: Aug. 19, 2004

(65) Prior Publication Data

US 2006/0037157 A1 Feb. 23, 2006

(51) Int. Cl.
*A46B 5/04* (2006.01)
*A61C 17/22* (2006.01)
(52) U.S. Cl. ............................. 15/28; 15/22.1; 15/22.2
(58) Field of Classification Search ................ 15/22.1, 15/22.2, 28, 167.1, 227
See application file for complete search history.

(56) References Cited

U.S. PATENT DOCUMENTS 1,645,965 A * 10/1927 Neumerkel ................... 15/227
4,628,949 A * 12/1986 Mas et al. .................... 132/308

* cited by examiner

*Primary Examiner*—Mark Spisich
(74) *Attorney, Agent, or Firm*—Jen-Feng Lee

(57) ABSTRACT

A toothbrush for the use of fingers to brush the teeth of infants or young children. While fingers work better than the traditional stick-type toothbrush in maneuvering around inside the mouth, the lack of vibrating/rotating in the bristle portion greatly diminished the flexibility of human fingers. Present invention provides the small-scale motion needed to rotate or otherwise move the bristle piece connected, by a flexible yet rigid cord, to a driving member, so that the brushing youngsters teeth are made more effective, resulting in better oral hygiene for infants and young children.

5 Claims, 2 Drawing Sheets

TOOTHBRUSH WITH MOVING BRISTLE

BACKGROUND OF INVENTION

The present invention relates generally to a toothbrush having moving bristle driven by motor means, to be maneuvered by adult's finger so that adults can more effectively message the gum and brush the teeth of infant or young children, resulting in better oral hygiene for youngsters.

It's generally not disputed that a parent's finger has the best sensitivity when used to brush children's teeth. Prior art patent, such as U.S. Pat. No. 4,134,172 (Oscar A. Arce) teaches the use of bristle at the of the finger-tip portion and reflects the value of using adult's finger as the mechanism upon which the brushing motion originates, instead of a run-of-the-mill stick-type toothbrush held in the palm.

However, because an adult's finger has limited small-scale mobility, such brushing may not be as effective as using an electric brush having enhanced bristle motion that helps to brush off food remnants stuck to children's teeth and in between gaps.

Present invention teaches to have the enhanced bristle motion of an electric brush and the sensitivity of an adult's finger and greatly promote the oral hygiene for children.

SUMMARY OF INVENTION

Regular run-of-the-mill electric brush, though having enhanced bristle motion for cleaning effectiveness, is limited in its maneuverability inside children's mouth. Present invention provides a simple and effective brush having moving bristle to be placed on an adult's finger tip and thus will have the benefits of good bristle motion and good maneuverability.

BRIEF DESCRIPTION OF DRAWINGS

The accompanying drawings, which are incorporated in and constitute a part of this specification, illustrate the preferred embodiment of the invention and together with the description, serve to explain the principles of the invention.

A brief description of the drawings is as follows.

DETAILED DESCRIPTION

Figure 1:
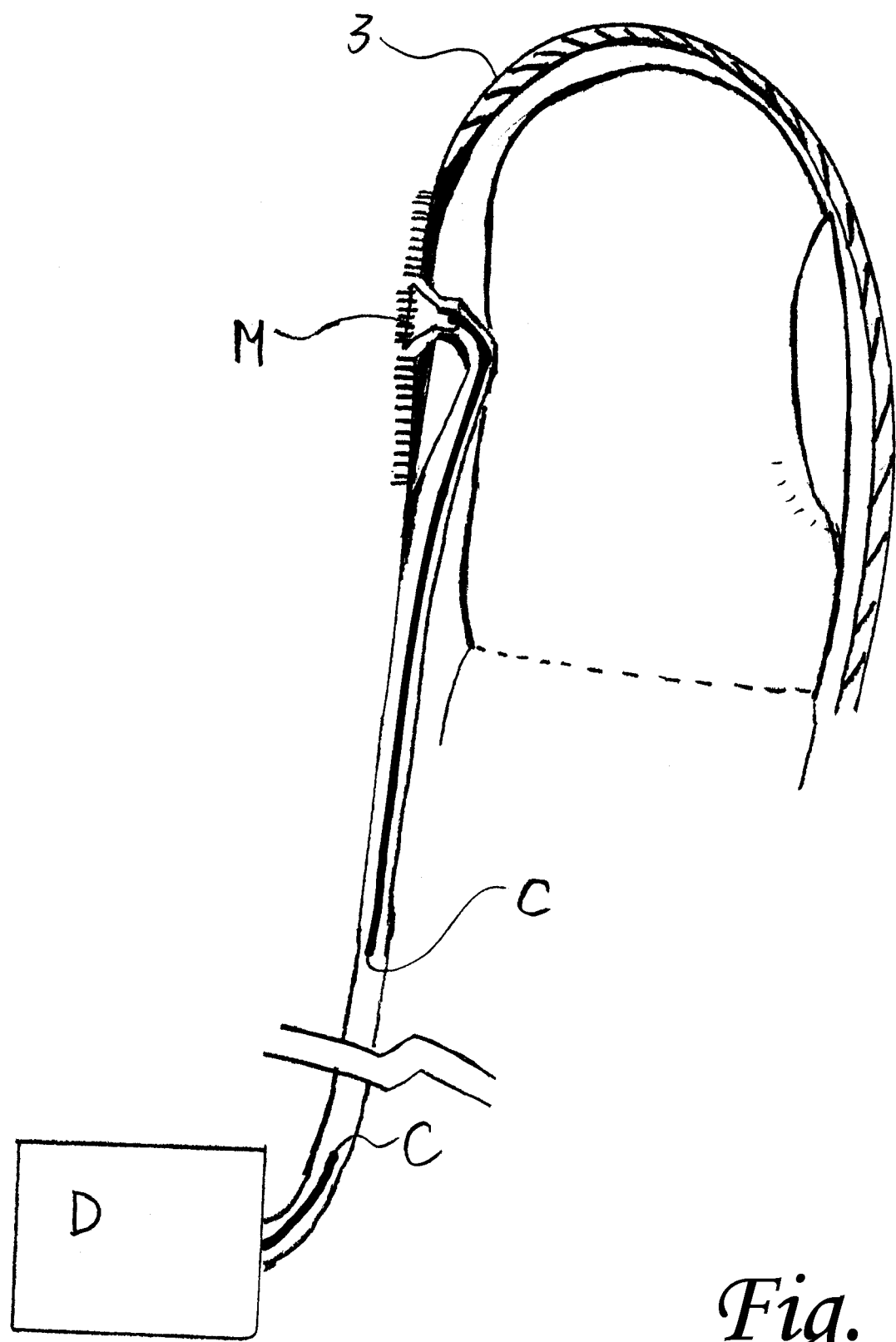
FIG. 1 shows the side view of present invention. M indicates the central rotating bristle portion driven by a cord C connected to a driving means and gear reduction means D.

FIG. 1 shows a finger capping piece 3 having some bristle around a hole, in the tip portion of said finger capping piece 3, to be worn over a person's finger. A bristle piece M is rotatably located into the hole, and is connected to a cord C, which is ultimately connected and driven by means D, which typically consists of an electrical motor and gear reduction means.

Depending on implementation, means D can also be a manual power mechanism such as the rack-and-pinion rotating shaft used on an ice cream scoop.

In FIG. 1, said cord C is rotatably placed inside a tube-like space formed along the side of said finger capping piece 3.

Driving means D can be implemented to be a cylindrical shape held in a person's palm or even strapped onto a person's wrist/arm, while the person can move his/her finger about inside a child's mouth to brush the child's teeth.

Finger capping piece 3 can be constructed of rubber or other suitable material, with reinforced portion built around the hole receiving bristle piece M and the wall behind the tube-like space touching adult's finger, so that bristle piece M can rotate when driven by cord C.

Cord C can be made from relatively stiff material, such as steel or other suitable material, so that it will carry the rotational movement from means D to the bristle piece M.

Figure 2:
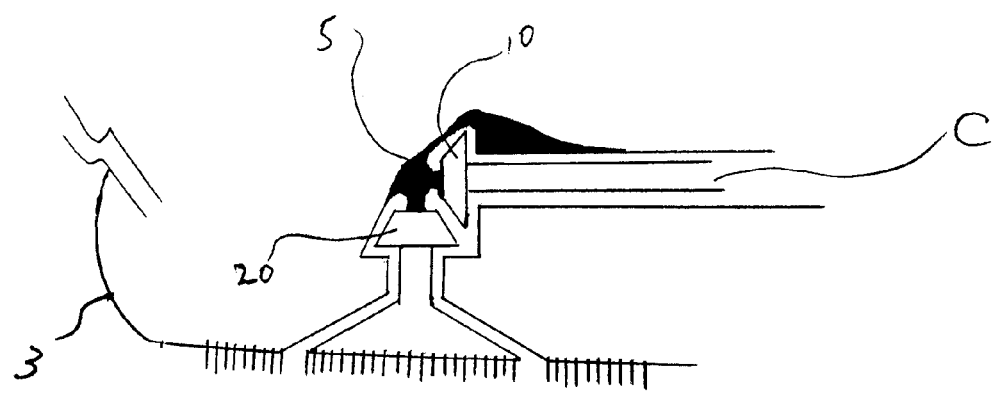
FIG. 2 shows the bristle portion M can be driven to rotate by use of bevel gears.

FIG. 2 shows the bristle piece M can be driven by cord C using bevel gears 10 and 20, securely held in place by holding piece 5.

Figure 3:
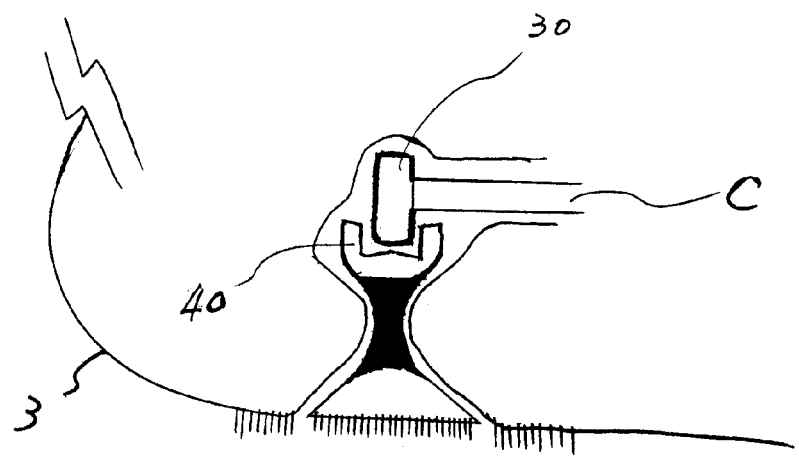
FIG. 3 shows the bristle portion M can be made into non-circular brushing motion by the use of a receptacle piece 40 and a cam piece 30 at the end of cord C.

FIG. 3 shows the bristle piece M can also move in a non-circular fashion when a cam piece 30 is used at end of cord C to push and jam the receptacle piece 40 at back end of bristle piece M. Cord C is connected to an off-center axial position of cam piece 30, so that when cord C is rotating, cam piece 30 generates a linear up-and-down motion to push and jam the bristle piece M around, and thus is effective in producing brushing motion. The center of receptacle piece 40 can be raised up a little bit, increasing the sliding-around motion of bristle piece M when the linear up-and-down motion is being exerted.

Children's edible tooth paste serves as natural lubricant for the motion of the bristle piece, whether the connection is made by cam piece 30, or bevel gears 10 and 20, or the direct linkage type as shown in FIG. 1.

The invention claimed is:

1. A toothbrush with moving bristle, comprising:
   a. a capping piece to be place on a person's finger having some bristle around a hole in the tip portion of said capping piece;
   b. a bristle piece rotatably located through the hole in the tip portion of said capping piece;
   c. a flexible but rigid cord connecting the back end of said bristle piece and placed inside a tube-like space built along the side of said capping piece; and
   d. a driving means providing rotating motion to said cord.

2. The toothbrush of claim 1, wherein said bristle piece is driven by said cord by the use of a pair of bevel gears.

3. The tooth brush of claim 1, wherein said bristle piece further having a receptacle piece at its back end, and is driven to move in a non-circular fashion, by a cam piece connected to said cord.

4. The toothbrush of claim 1, wherein said driving means consist of an electrical motor coupled with gear reduction means to reduce said cord's rotational speed but increase its rotational torque.

5. The toothbrush of claim 1, wherein said driving means consist of a rack-and-pinion type shaft that can be powered by a person's fingers and palm to drive and rotate said cord.

* * * * *